United States Patent [19]

Makela et al.

[11] Patent Number: 4,652,518

[45] Date of Patent: Mar. 24, 1987

[54] DIAGNOSING CHLAMYDIA INFECTIONS WITH RE-LIPOPOLYSACCHARIDE COMPLEXED TO CARRIER OR ANTIBODY THERETO

[75] Inventors: Pirjo H. Makela; Maija K. Leinonen; Marjatta H. Nurminen-Kalliokoski; Pekka A. I. Saikku, all of Helsinki, Finland

[73] Assignee: Orion Corporation, Ltd., Helsinki, Finland

[21] Appl. No.: 507,788

[22] Filed: Jun. 24, 1983

[30] Foreign Application Priority Data

Jul. 2, 1982 [FI] Finland ................................. 822348

[51] Int. Cl.$^4$ .................. G01N 33/53; G01N 33/546; G01N 33/561; G01N 33/571

[52] U.S. Cl. ........................................ 435/7; 435/29; 435/879; 436/510; 436/515; 436/516; 436/519; 436/520; 436/522; 436/533; 436/534; 436/543; 436/547; 436/811; 436/823; 530/387; 536/1.1

[58] Field of Search ............................ 435/7, 29, 879; 436/510, 515, 516, 519, 520, 522, 533, 534, 543, 547, 811, 823; 536/1.1; 530/387

[56] References Cited

U.S. PATENT DOCUMENTS

| | | |
|---|---|---|
| 4,039,657 | 8/1977 | McAleer et al. |
| 4,096,035 | 6/1978 | Machlowitz |
| 4,118,469 | 10/1978 | Caldwell et al. |
| 4,267,170 | 5/1981 | Seawell |
| 4,271,146 | 6/1981 | Seawell |
| 4,310,455 | 1/1982 | Bahl ............................ 436/823 |
| 4,397,959 | 8/1983 | Hechemy ...................... 436/509 |
| 4,497,899 | 2/1985 | Armstrong .................... 436/510 |

FOREIGN PATENT DOCUMENTS

| | | |
|---|---|---|
| 17460 | 10/1980 | European Pat. Off. |
| 50424 | 4/1982 | European Pat. Off. |
| 2047889 | 12/1980 | United Kingdom |

OTHER PUBLICATIONS

Makela, P. H. et al., Annual Review of Genetics, vol. 3, 291-322, (1969).

Kuusi, N. et al., Infection and Immunity, 34(2), 328-332, (1981).

Kohler, G. et al., Nature, 256, 495-497, (Aug. 7, 1975).

M. Nurminen et al., Science, 220 (4603), 1279-1281, (1983).

Chemical Abstracts, I, 97:3214m, (1982).
Chemical Abstracts, II, 97:213914r, (1982).
Chemical Abstracts, III, 97:214132w, (1982).
Chemical Abstracts, IV, 98:51651u, (1983).

Luderitz et al., *Comprehensive Biochemistry*, vol. 26A, pp. 105-228, N. Florkin & E. H. Stotz, Eds., Elsevier, Amsterdam, (1968).

Makela & Stocker in, *Genetics as a Tool in Microbiology*, Glower & Hopwood, Eds., Soc. Gen. Microbiol. Symp., 31, Cambridge University Press, (1981).

Luderitz et al., *Current Topics in Membranes and Transport*, vol. 17, pp. 79-151, (1982).

Laemmli in, *Nature*, vol. 227, pp. 680-685, (1970).

Tsai & Frasch, *Anal. Biochem.*, vol. 119, pp. 115-119, (1982).

Towbin et al., *Proc. National Acad. Sciences*, vol. 76, pp. 4350-4354, (1979).

Nurminen et al., *J. Bact.*, vol. 127, pp. 941-955, (1976).

Wilkinson et al., *Journal of General Microbiol.*, vol. 70, pp. 527-554, (1972).

Luderitz et al., *Annals of N.Y. Academy of Sciences*, vol. 133, pp. 349-374, (1966).

(List continued on next page.)

*Primary Examiner*—Sidney Marantz
*Attorney, Agent, or Firm*—Brumbaugh, Graves, Donohue & Raymond

[57] ABSTRACT

A preparation for the detection of chlamydial infections using lipopolysaccharide of Re-lipopolysaccharide mutants of gram-negative bacteria. The lipopolysaccharide preparation is used in the production of group-specific antibodies to chlamydiae for diagnostic purposes or for the demonstration of antibodies to chlamydial group antigen in specimens.

26 Claims, 3 Drawing Figures

OTHER PUBLICATIONS

*Escherichia coli*, Mayer et al., *European Journal of Biochem.*, vol. 66, pp. 357–368, (1976).

Kotelko et al., *Journal of Hyg. Epidemiol. Microbiol. Immunol.*, vol. 21, pp. 271–284, (1977).

Schlecht & Westphal, *Infections-krankenheiten und Hygiene*, vol. 1, Orig. 200, pp. 241–259, (1966).

Galanos et al., the *European Journal of Biochem*, vol. 9, pp. 245–249, (1969).

Westphal et al., *Methods in Carbohydrate Chemistry*, Editors R. L. Whisler, J. N. BeMiller & M. L. Wolfram, vol. 5, p. 83.

*Handbook of Micromethods for the Biological Sciences*, Keleti & Lederer, Eds., pp. 133–135, (1974).

Koskela and Leinon in, *Ped. Inf. Dis.*, vol. 1, pp. 245–252, (1982).

Koskela and Leinon, *Journal of Clinical Pathology*, vol. 34, pp. 93–98, (1981).

*Journal of Clinical Microbiology*, vol. 11, pp. 135–140, (1980), Leinon.

*Handbook of Experimental Immunology*, ed. D. M. Weir, Chapter 19, Blackwell Scientific Publications, Oxford, (1978).

*Handbook of Micromethods for the Biological Sciences*, Keleti & Lederer, Eds., pp. 134–135, (1974).

*Journal of Medical Virology*, vol. 3, pp. 245–252, (1979), P. Vaananen.

*Journal of Virol. Methods*, vol. 4, pp. 117–126, (1982), P. Vaananen.

*Rapid Virus Diagnosis, Application of Immunofluorescence*, Gardner & McQuillan, Eds., Butterworths, London, p. 60.

Goodfriend et al., *Science*, vol. 144, pp. 1344–1346, (1964).

DIAGNOSING CHLAMYDIA INFECTIONS WITH RE-LIPOPOLYSACCHARIDE COMPLEXED TO CARRIER OR ANTIBODY THERETO

BACKGROUND OF THE INVENTION

The present invention relates to a novel preparation for the detection of chlamydial infections using lipopolysaccharides of Re-lipopolysaccharide mutants of gram-negative bacteria.

Chlamydiae are very small, obligately intracellular bacteria which infect birds, man and other mammals. The chlamydiae are classified into two species, *Chlamydia trachomatis* and *Chlamydia psittaci*. *Chlamydia trachomatis* has a high degree of host specificity, being almost completely limited to man; it causes ocular and genitourinary infections of varying severity. In contrast, *Chlamydia psittaci* strains are rare in man but are found in birds and in wild and domestic animals. *C. psittaci* is a cause of abortion and epidemics of diarrhea in animals.

While antichlamydial drug therapy exists, many chlamydial infections go untreated because of the limitations connected with the available diagnostic methods. The best known serological methods used for diagnosis of chlamydiae are complement fixation tests, using chlamydial glycolipid (also called a group antigen), counterimmunoelectrophoresis assays and immunofluorescence assays. These methods are described in U.S. Pat. No. 4,118,469, European Patent No. 17,460 and British Patent No. 2,047,889. The isolation of chlamydial antigens and their use as vaccines are described in U.S. Pat. Nos. 4,118,469, 4,039,657, 4,096,035, 4,271,146 and 4,267,170.

A major problem in diagnosing chlamydial infections resides in culturing the chlamydiae. As obligate intracellular bacteria, chlamydiae must be cultured in living cells, e.g. tissue culture or egg preparation, necessitating laboratories which specialize in cell culture. The methods of culturing chlamydiae are characterized by low yields and inevitable contamination by extraneous substances, such as non-chlamydial proteins, from the associated living cells. Although the presence of contaminants is trivial conceptually, such contaminants are important in serologic methods since even trace levels of contaminants can elicit the formation of detectable amounts of antibody. This problem has necessitated the need for control antigens to assess nonspecific reactions in chlamydial serologic methods. The preparation of chlamydial antigen albeit contaminated with extraneous substances is time-consuming, expensive and even possibly risky to the health of the researcher.

If two different antigen molecules happen to have one or more functional groups in common, then these antigens are said to cross-react. Cross-reaction is a tool which has been utilized for classifying groups of closely related bacteria. For example, the 1500 or more varieties of salmonellae have been arranged into serologic groups by cross-reactions, i.e. the antiserum of a strain of a particular group reacts with other strains of that group. The common groups or antigenic determinants responsible for these group-specific reactions are short sequences of particular sugar residues. Cross-reacting groups need not be identical; they only need to be sufficiently similar. For example, antibodies to m-azobenzenesulfonate cross-react with m-azobenzenearsonate.

Rough (R) mutants are a well known class of bacterial mutants (Luderitz et al., *Comprehensive Biochemistry*, Vol. 26A, pp. 105–228, M. Florkin & E. H. Stotz, Eds., Elsevier, Amsterdam (1968); Makela & Stocker, *Annu. Rev. Genetics*, Vol. 3, pp. 291–322 (1969); Makela & Stocker in *Genetics As a Tool in Microbiology*, Glower & Hopwood, Eds., *Soc. Gen. Microbiol. Symp.* 31, Cambridge University Press (1981)) in which a step in the biosynthesis of LPS is defective, thereby blocking the completion of the molecule. The R mutants are classified into chemotypes according to their LPS structure (FIG. 4 and pages 156–171 in Luderitz et al. 1968, and FIG. 4 in Luderitz et al., *Current Topics In Membranes and Transport*, Vol. 17, pp. 79–151 (1982). In this classification, a chemotype of Re or a "Remutant" is defined as a mutant whose LPS consists of lipid A and KDO (3-deoxy-D-manno-octulosonic acid, previously called 2-keto-3-deoxy-octonate) with no other monosaccharide substituents. For this reason Re mutants are often referred to as "heptoseless" since they are devoid of even heptose, the monosaccharide that in most LPS is the next unit linked distal to KDO. Such Re mutants were first described in the genus Salmonella (both *S. typhimurium* and *S. minnesota*) but have been later found in other species (*Escherichia coli* and *Proteus mirabilis*), and can probably be isolated from many others because the LPS structure in the immediate vicinity of lipid A is very conservative throughout the gram-negative bacteria (Luderitz et al. 1982).

It is an object of this invention to detect antibodies to chlamydiae by using Re-lipopolysaccharide (Re-LPS) from Re-mutants of gram-negative bacteria.

Another object of this invention is to detect chlamydiae by using antibodies to Re-LPS from Re-mutants of gram-negative bacteria.

It is also an object of this invention to eliminate the drawbacks and problems described above which are associated with the culturing of chlamydiae.

It is a further object of this invention to eliminate the need for control antigens.

SUMMARY OF THE INVENTION

It has been found that antibodies to chlamydial glycolipid cross-react with the Re-lipopolysaccharide of Re-lipopolysaccharide (Re-LPS) mutants of gram-negative bacteria and that chlamydial glycolipid antigen cross-reacts with the anti-Re-lipopolysaccharide antibodies. A preparation according to the invention, the so-called Re-LPS, can be used in the production of group-specific antibodies of chlamydiae for diagnostic purposes or for the demonstration of antibodies to chlamydial group antigen in specimens, such as serum, feces, or nasal, laryngeal or urethral mucus. The preparation can be used as antigen in serological methods commonly used in diagnosis of chlamydial infections, such as the complement fixation test, counter-immunoelectrophoresis method, passive hemagglutination, hemolysis-in-gel (HIG), enzyme immunoassay (EIA), immunofluorescence (FIA) and radioimmunoassay (RIA) methods. The use of the preparation is not limited to the methods described above but can, in principle, be used in all serological or immunological methods, in which antibodies to group-specific antigen of chlamydia need to be demonstrated. Antiserum to group specific chlamydial antigen can be produced directly by immunization with a Re-mutant of a gram-negative bacterium, without isolation of the Re-lipopolysaccharide.

The Re-LPS of the present invention are easy and inexpensive to produce. It is suitable for mass production, and can be used in diagnosis and in immunological and serological methods in many different ways. Since the Re-LPS of the invention is chemically pure, control antigens are not needed in order to determine the interference of extraneous material from the tissue culture or egg preparations.

DESCRIPTION OF THE PREFERRED EMBODIMENTS

The preparation of the present invention contains a Re-lipopolysaccharide isolated from Re-lipopolysaccharide mutants of gram-negative bacteria.

Gram-negative bacteria contain a lipopolysaccharide having the following general structure:

(I)

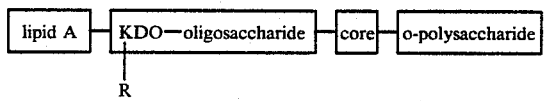

The lipid A component illustrated in (I) contains glucosamine disaccharide, substituted at the hydroxyl group with fatty acids, 4-aminoarabinose phosphate and diphosphorylethanolamine, substituted at the amino group with fatty acids. The core component is a polysaccharide which is connected to the lipid A by a KDO-oligosaccharide component composed of two or three KDO-molecules, one of which can be substituted with an R component. The R is selected from the group consisting of hydrogen, a phosphate group and a diphosphorylalkanolamine group, and preferably a diphosphorylethanolamine group. The o-polysaccharide component is a (monosaccharide)$_n$ where n is an integer from zero to infinity. While the structures of the lipid A, the core and the o-polysaccharide components vary in different bacterial strains, the structure of the KDO-oligosaccharide component containing two or three KDO-molecules usually remains fairly constant. KDO is 3-deoxy-D-manno-octulosonic acid having a structure of

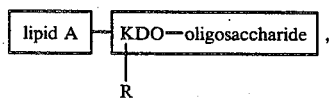

Representative gram-negative bacteria, e.g. the Salmonella group, contain a core of at least the components of glucosamine, glucose, galactose and heptose. Re-LPS mutants of such gram-negative bacteria produce a Re-LPS which lacks the core and o-polysaccharide components. The Re-LPS, which is represented as (II)

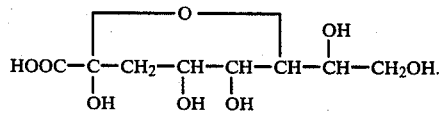

where lipid A, KDO-oligosaccharide and R have the same meanings as above, cross-reacts with chlamydial antibodies.

Figure 1:
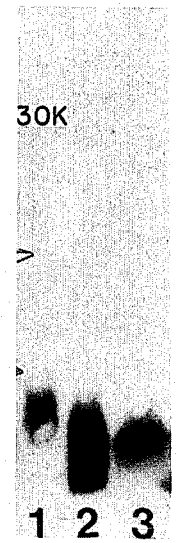

Using conventional chemical analysis, the molecular weight of a Re-LPS is about 3000. When the Re-LPS is subjected to electrophoresis in an 15% sodium dodecyl-sulfate-polyacrylamide gel (the SDS-PAGE method as described by Laemmli in *Nature*, Vol. 227, pp. 680–685 (1970), the speed of migration of the Re-LPS (as indicated by the final position of the band after electrophoresis) is similar to that of the glycolipid group antigen of *Chlamydia trachomatis*. The speed of migration of the Re-LPS is also clearly different from the speed of migration of the LPS of chemotype Rb$_2$ which has a molecular mass of approximately 4000 d and which has 6 monosaccharides of the core in addition to the lipid A-KDO-oligosaccharide (see Luderitz et al. 1982 as cited above for the Rb$_2$ structure). The LPS bands can be visualized in the gel after staining with silver nitrate (Tsai & Frasch, *Anal. Biochem.*, Vol. 119, pp. 115–119 (1982) or with immunoblotting (Towbin et al., *Proc. National Acad. Sciences*, Vol. 76, pp. 4350–4354 (1979). Such a gel after silver nitrate staining is shown in FIG. 1 in which lane 1 is Rb$_2$-LPS from *S. typhimurium* Rb$_2$ mutant strain SH 5014 (Nurminen et al., *J. Bact.*, Vol. 127, pp. 941–955, (1976)), lane 2 is Re-LPS from *S. typhimurium* Re mutant strain SL 1102, and lane 3 is glycolipid from *Chlamydia trachomatis*. While the samples were applied on top of the gel, only the lower part of the gel where the small molecular weight LPS band is shown.

While some of the fatty acids and 4-aminoarabinose phosphate may be removed from the Re-LPS by treatment with a weak alkali (0.16 N NaOH, 1 h, 56° C.), the KDO component remains attached to the Re-LPS. When the Re-LPS of (II) is treated with a weak alkali, it retains its immunogenic properties and therefore can be used advantageously to demonstrate antibodies to chlamydial group antigen in various immunological and serological methods. When the Re-lipopolysaccharide is boiled in weak acid (0.1 N HCl), the KDO substituents detach, thereby destroying the immunogenic determinants needed for chlamydial diagnosis.

The antiserum produced to Re-lipopolysaccharides or whole Re-mutant bacteria in experimental animals cross-reacts with glycolipid antigen isolated from chlamydiae species.

Re-lipopolysaccharide mutants (heptoseless) are used to synthesize the Re-LPS represented in (II). The Re-mutants are produced by well known methods from the gram-negative parent bacteria which are capable of synthesizing the LPS represented in (I). The Re-mutants can be derived from several readily available gram-negative bacteria. The Re-mutants used in this invention are as follows: *Salmonella typhimurium* (Re-mutant) (SL 1102), Wilkinson et al., *Journal General Microbiol.* Vol. 70, pp. 527–554 (1972); *Salmonella minnesota* (Re-mutant R595) (SH 320), Luderitz et al., *Annals of N.Y. Academy of Sciences*, Vol. 133, pp. 349–374 (1966); *Escherichia coli* K-12 (Re-mutant D21f2) (EH 237), Mayer et al., *European Journal of Biochem.*, Vol. 66, pp. 357–368 (1976) and *Proteus mirabilis* (Re-mutant R45), Kotelko et al. *Journal of Hyg. Epidemiol. Microbiol. Immunol.*, Vol. 21, pp. 271–284 (1977). These Re-mutants are readily available from the research groups mentioned in these publications or from the National Public Health Institute in Helsinki. The lipopolysaccharide preparation of the invention can also be produced from gram-negative bacteria other than those mentioned above, provided the gram-negative bacteria and their Re-mutants both produce the specific lipopolysaccharides described above.

The gram-negative bacteria used in this invention do not require special nutrients in the culture media. Since the bacteria in which Re-mutation has occurred are very sensitive to detergents, bile acids and poisons, Re-mutants pose little problems outside laboratory conditions.

The bacteria suitable for use in this invention can be grown on a variety of media, such as an enriched Salmonella-agar, described by Schlecht and Westphal in Zentralblatt fur Bakteriologie, Parasitenkunde, *Infections-krankenheiten und. Hygiene*, Vol. 1, Orig. 200, pp. 241–259 (1966). The Re-mutants of the invention are grown overnight on enriched Salmonella-agar and are then collected with water. Then the cells are centrifuged at 5000 rpm for about 10 min. The cell pellet is washed with distilled water and recentrifuged at 5000 rpm for about 10 min. The use of distilled water at this phase is essential for the successful isolation of lipopolysaccharide. Although the isolation of the lipopolysaccharide from the Re-mutant can advantageously be carried out according to the method described by Galanos et al. in the *European Journal of Biochem.*, Vol. 9, pp. 245–249 (1969), other well known methods may also be used, with good yields, see, for example, Westphal et al. in *Methods in Carbohydrate Chemistry*, Editors R. L. Whistler, J. N. BeMiller and M. L. Wolfram, Vol. 5, p. 83. The LPS can be treated with alkali as described in *Handbook of Micromethods for the Biological Sciences*, Keleti & Lederer, Eds., pp. 133–135 (1974).

In accordance with the invention, the following description of specific test procedures is illustrative: Re-mutant R595 of *Salmonella minnesota* bacterium (Luderitz et al., 1966 as cited above).

A. Culture of *Salmonella minnesota*

The Re-mutant R 595 of *Salmonella minnesota* was grown overnight at 37° C. on enriched Salmonella agar plates (Schlecht & Westphal, 1966 as cited above), prepared from 10 l of enriched Salmonella agar. The bacteria were collected with about 500 ml of distilled water, transferred into a centrifuge bottle and centrifuged at 5000 rpm for about 10 min. The pellet of cells was resuspended in distilled water and centrifuged at 5000 rpm for about 10 min. The pellet of cells was freeze dried. The yield was about 30 g.

B. Isolation of Re-lipopolysaccharide (Galanos et al., 1969 as cited above)

The lipopolysaccharide was extracted from the freeze-dried pellet using a phenol:chloroform:petrolether mixture (2:5:8) at 0° C. The chloroform and petrolether were removed by evaporation and the lipopolysaccharide was precipitated by distilled water. The lipopolysaccharide was purified by dissolving the precipitate in distilled water at 45° C. and centrifuging at 100,000×g. The lipopolysaccharide was freeze dried and stored at room temperature. The yield of lipopolysaccharide was about 5% of the bacterial dry weight.

C. Alkali Treatment of the Re-lipopolysaccharide 10 mg of the Re-lipopolysaccharide isolated in paragraph B was solubilized in 1 ml of 0.25 M sodium hydroxide. The solubilized Re-LPS was incubated at 56° C. for 60 min and allowed to cool to room temperature. Then this material was centrifuged at 2000 rpm for 15 min at 4° C. The resultant supernatant was collected and neutralized with 1 N acetic acid. The neutralized material was dialyzed against water overnight and the dialyzed material was freeze-dried.

D. Immunization with the isolated lipopolysaccharide

Since a pure lipopolysaccharide elicits weak immunological responses, the lipopolysaccharide was complexed with a carrier molecule, such as a protein, to enhance the immunological response. For example, 1 mg of Salmonella-porin-protein (carrier) and 0.1 mg of Re-lipopolysaccharide were mixed in 5 ml of 0.25% sodium lauryl sulfate (SDS). After the complexation occurred, the immunogen was dialyzed to remove the SDS. This method was described by Kuusi et al. in *Inf. Imm.*, Vol. 34, pp. 328–332 (1981).

Antibodies against Re-lipopolysaccharide were produced by conventional immunization methods. Rabbits were inoculated with 0.5 ml of the dialyzed immunogen at four sites on each rabbit. All injections were subcutaneous. A booster inoculation of 0.5 ml of the immunogen was given 14 days after the primary inoculation. Serum was collected from the rabbits 10 days after the last injection.

E. Immunization with whole bacteria

*Salmonella minnesota* were grown in broth until the bacteria entered the logarithmic growth phase. The bacteria were collected by centrifugation and washed once with physiological saline. The bacteria were suspended in physiological saline at a concentration of $10^{10}$ bacteria/ml and were inactivated by heating for 1 hour at 100° C. and by adding 0.5% formalin. Rabbits were inoculated with 0.5 ml of the inactivated bacteria at four sites on each rabbit. Booster inoculations of 0.5 ml were given 7 times at one week intervals after the primary inoculation. Serum was collected 10 days after the last injection.

The method described in paragraph A can be utilized to culture Re-mutants prepared from other gram-negative bacteria. Antisera to these Re-mutants can be produced in accordance with the method described in paragraph E. The lipopolysaccharide can be isolated from the bacteria in accordance with the method described in paragraph B, and the antisera to the lipopolysaccharide can be produced in accordance with the method described in paragraph D.

The following examples demonstrate the applicability of preparation of the invention in the detection of chlamydiae or chlamydial antibodies.

EXAMPLE 1

The cross-reactions of antibodies to Re-mutants of gram-negative bacteria were investigated using the enzyme immunoassay (EIA) method described by Koskela and Leinonen in *Ped. Inf. Dis.*, Vol. 1, pp. 245–252 (1982). The antigen employed in the EIA method was the glycolipid isolated from chlamydiae. Antiserum to chlamydial glycolipid was prepared by the immunization of rabbits with Salmonella Re-mutant strains (*S. typhimurium, S. minnesota*) and Re-LPS-porin complex. The antibody titers against chlamydial glycolipid in *S. typhimurium* and *S. minnesota* Re-mutant antisera, as determined by the EIA method, are shown in Table I.

TABLE I

| Immunogen | EIA titer |
|---|---|
| *S. typhimurium* Re | 8500 |
| *S. typhimurium* Re | 1000 |
| *S. minnesota* Re | 2000 |

TABLE I-continued

| Immunogen | EIA titer |
| --- | --- |
| S. minnesota Re-LPS-porin | 1750 |
| Normal serum | <100 |
| S. typhimurium Rd₂* | <100 |

*One heptose residue of the LPS core component is present in the mutant in addition to the lipid A KDO-oligosaccharide.

The results shown in Table 1 indicate that antisera prepared by the immunization of rabbits with Re-mutant strains (S. typhirmurium and S. minnesota) and Re-LPS-porin complex contain high-titer antibodies against chlamydial glycolipid. The chamydial glycolipid did not cross-react with normal serum or with antiserum to the S. typhirmurium mutant of chemotype Rd$_2$, which has one sugar residue of the LPS core left.

EXAMPLE 2

Lipopolysaccharide preparations (Re-LPS) of the invention were employed as antigens to detect chlamydial antibodies.

A. Enzyme Immunoassay Method and Other Solid Phase Methods

Microtitre enzyme immunoassay plates (A/S Nunc., Roskilde, Denmark) were coated using the following Re-LPS concentrations: 1, 5, 10 and 20 μg/1 ml of phosphate-buffered saline solution at pH of 7.4. The plates were inoculated and incubated at 37° C. overnight. The EIA determinations were carried out and the results (EIA titers) calculated as described in detail by Koskela et al. in *Journal of Clinical Pathology*, Vol. 34, pp. 93–98 (1981) and by Koskela et al., in *Ped. Inf. Dis.*, Vol. 1, pp. 245–252 (1982). The alkaline phosphatase labelled anti-immunoglobulin conjugates were commercial preparations of anti-human IgG, IgM and IgA, anti-rabbit IgG and anti-mouse IgG, all supplied by Orion Diagnostica, Helsinki, Finland.

The optimal concentrations of Re-LPS or alkali-treated Re-LPS giving the highest EIA titer in rabbit antiserum to Re-mutant and also a negative result in non-immunized rabbit serum was 10 μg/ml. This Re-LPS concentration was used for coating the plates in later studies.

Rabbits were immunized with chlamydiae as described in Paragraph E. Antisera from these rabbits were tested against Re-LPS isolated from four different bacteria using the EIA method. The EIA-antibody titers against Re-LPS preparations in chlamydial antisera, or in rabbit antiserum to S. minnesota Re-mutant or in normal rabbit serum are shown in Table II.

TABLE II

| Antiserum | EIA titer to LPS isolated from Re-mutant of | | | |
| --- | --- | --- | --- | --- |
| | S. typhim. | S. minnes. | E. coli | Proteus |
| Chlamydia 1 | 2150 | 2111 | 2180 | 2100 |
| Chlamydia 2 | 2750 | 2600 | 1920 | 2760 |
| Chlamydia 3 | 1400 | 1830 | 1250 | 230 |
| S. minnesota | | | | |
| Re-mutant | 490 | 140 | 940 | 1370 |
| NRS* | <100 | <100 | <100 | <100 |

*NRS = normal rabbit serum

Monoclonal mouse antibodies to chlamydiae were produced by the hybridoma technique described by Kohler et al. in *Nature*, Vol. 256, pp. 495–497 (1975). Monoclonal antibodies react in the EIA test with the chlamydial glycolipid and also react with Re-LPS. The EIA reactivity of monoclonal antibodies to chlamydial glycolipid, to Re-LPS of S. typhimurium and to the same Re-LPS after alkali treatment (as described in C above) are shown in Table III.

TABLE III

| Monoclonal antibody | EIA reaction, when the antigen is | | |
| --- | --- | --- | --- |
| | Chlamydial glycolipid | Re-LPS from S. typhimurium | The same Re-LPS after alkali treatment |
| 1 | + | + | + |
| 2 | + | + | + |
| 3 | + | + | + |
| 4 | + | + | + |

Since monoclonal antibodies are specific to one antigenic determinant, the reactions of the monoclonal antibodies with chlamydial glycolipid and with Re-LPS indicate a common antigenic structure in the chlamydial glycolipid and Re-LPS.

Radio- and fluoroimmunoassays (RIA and FIA) can also be used instead of EIA since these assays differ from EIA only by the label of the second antibody (e.g. radioisotope in RIA, fluorochrome in FIA and enzyme in EIA).

B. Counterimmunoelectrophoresis (CIE)

Figure 2:
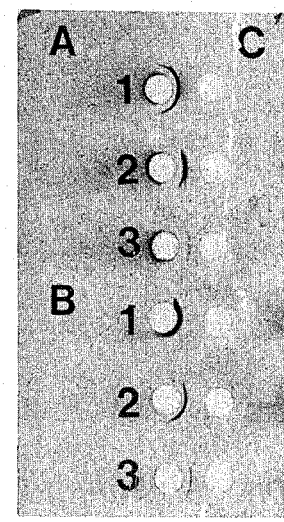

The antiserum from a rabbit immunized with Chlamydia (Chlamydia 1 of Table II) was tested against Re-LPS (from S. typhimurium SL 1102) and alkali-treated Re-LPS by using CIE-method (Leinonen, *Journal of Clinical Microbiology*, Vol. 11, pp. 135–140 (1980)). The results are shown in FIG. 2. Re-LPS (A) and alkali-treated Re-LPS (B) in three different concentrations 100 μg/ml, 10 μg/ml and 1 μg/ml (1, 2 and 3) form a clear-cut precipitin line with chlamydial antiserum (C).

C. Double Immunodiffusion

Figure 3:
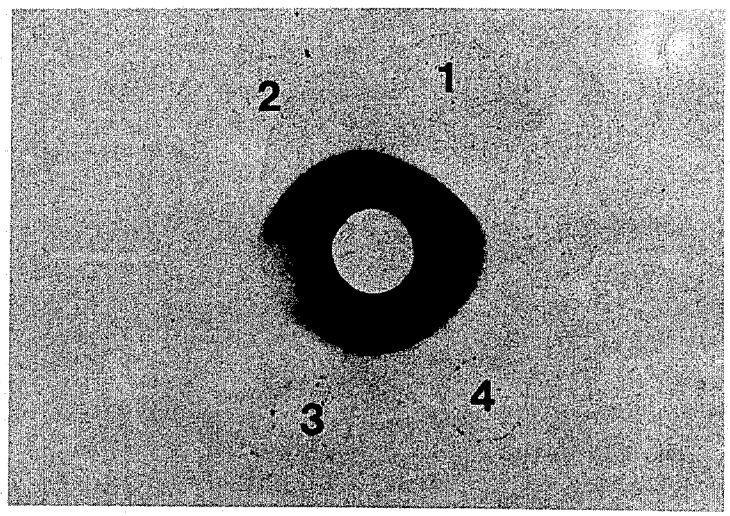

The antiserum from a rabbit immunized with Chlamydia (Chlamydia 1 of Table II) was tested against Re-LPS (from S. typhimurium SL 1102) and alkali-treated Re-LPS by using double immunodiffusion (FIG. 3). The wells were punched out from the 0.9% agarose gel, containing 0.15% deoxycholate (DOC). The wells contained 100 μg/ml of 0.15% DOC of chlamydial glycolipid (1,4), RE-LPS (2) and alkali-treated Re-LPS (3). The center well contained chlamydial antiserum. The precipitation lines against Re-LPS, alkali-treated Re-LPS and chlamydial glycolipid fused showing the reaction of identity (according to Ouchterlony and Nilsson, *Handbook of Experimental Immunology*, ed. D. M. Weir, Chapter 19, Blackwell Scientific Publications, Oxford (1978)).

D. Passive Hemagglutination

Sheep red blood cells were sensitized with Re-LPS (from S. typhimurium SL 1102) or with the alkali-treated Re-LPS as described (*Handbook of Micromethods for the Biological Sciences*, Keleti & Lederer, Eds., pp. 134–135 (1974)). The washed cells were suspended in phosphate buffered saline to a 0.5% suspension. 25 μl of this suspension were mixed with 75 μl of serial dilutions of the antisera to be tested in U-shaped wells of a microtiter plate. The agglutination was read by the naked eye after incubation at 37° C. for 30 minutes. Positive agglutinations were not observed with a normal rabbit serum, whereas the rabbit anti-chlamydial serum (Chlamydia 1 of Table II) agglutinated these cells in a high titer (Table IV). Untreated sheep red cells were not agglutinated.

TABLE IV

Passive hemagglutination titers with sheep red blood cells sensitized with Re-LPS.

| Serum | Sensitized with Re-LPS | Sensitized with alkali-treated Re-LPS | Unsensitized |
|---|---|---|---|
| Chlamydia 1 | 1024 | 256 | <2 |
| Normal rabbit | <2 | <2 | <2 |

E. Hemolysis in gel

Chicken red blood cells were sensitized with the alkali-treated Re-lipopolysaccharide of *S. typhimurium* SL 1102 as described in D above. The Re-LPS-treated red cells were mixed with melted agarose and complement, poured into plastic dishes and allowed to solidify as a gel plate as described by Vaananen and Vaheri in the *Journal of Medical Virology*, Vol. 3, pp. 245–252 (1979) and by Vaananen in the *Journal of Virol. Methods*, Vol. 4, pp. 117–126 (1982). Wells of a diameter of 2 mm were then punched in the gels. 6 μl of heat inactivated (56° C. for 30 min.) human sera were applied to the wells. The plate was incubated overnight at 37° and the diameters of the hemolytic zones were measured. The results were compared with the results obtained by the antichlamydial indirect fluorescence antibody test (IFAT), described by Weller and Coons in the *Proc. Soc. Exp. Biol. Med.*, Vol. 86, p. 789 (1954) and in *Rapid Virus Diagnosis, Application of Immunofluorescence*, Gardner and McQuillan, Eds., Butterworths, London p. 60), the routine method of measuring chlamydial antibodies in human sera. The results obtained by these methods (HIG and IFAT) are in good agreement as shown in Table V.

TABLE V

HIG Assay For Anti-Re in Human Sera (the chicken red cells were sensitized with alkali-treated Re-LPS and compared with anti-chlamydia IFAT).

| Human Serum | Methods used HIG diameter (mm) | IFAT (titer) |
|---|---|---|
| normal | 0 | <16* |
| patient | 6 | 256 |

*<16 means a negative result

F. Latex-Agglutination

Covalent fixation of the Re-lipopolysaccharide (from *S. typhimurium* SL 1102) and alkali-treated Re-lipopolysaccharide to latex particles was based on the use of water soluble carbodiimide (CDI) as described by Goodfriend et al. in *Science*, Vol. 144, pp. 1344–1346 (1964) as follows:

(a) 0.5 ml of carboxylated polystyrene latex particles (0.8 μm diameter, 100 g/l, Estapor, Rhone-Poulenc, Courbevoie, France) were washed two times in 5 ml of isotonic saline buffered by borate (20 mmol/l, BBS, pH 8.1), centrifuged and resuspended in 1 ml of this buffer;

(b) the latex suspension was activated by being stirred for 45 min at room temperature with 25 mg of 1-ethyl-3-dimethylaminopropyl-carbodiimide hydrochloride (Sigma Chemical Co.);

(c) after centrifugation and resuspension in 1 ml of BBS, the activated latex was incubated overnight at room temperature with gentle agitation with different amounts (150 μg, 250 μg, 300 μg and 500 μg) of Re-LPS and alkali-treated Re-LPS;

(d) after incubation, 250 μl of 1% bovine serum albumin in glycine buffered saline (GBS-BSA, pH 8.2) was added and the latex was centrifugated, washed three times with GBS-BSA, resuspended in 5 ml of GBS-BSA and sonicated for a few seconds; and (e) the latex reagents were stored at 4° C.

The rabbit anti-chlamydia serum (Chlamydia 1 of Table II) was tested for its ability to agglutinate latex particles. A normal rabbit serum served as a control. The latex tests were performed by mixing 25 μl of the antiserum or its dilutions and 25 μl of the latex reagent on a glass slide. After tilting for 2 min the slides were examined against a dark background for agglutination. The results are shown in Table VI.

TABLE VI

Latex Agglutination Titers of Rabbit Sera with Particles Sensitized with Re-LPS

| Latex-reagent coated with | SERUM Chlamydia 1 | NRS |
|---|---|---|
| Re-LPS | 80 | 0 |
| Alkali-treated Re-LPS | 80 | 0 |
| Neither | 0 | 0 |

EXAMPLE 3

Use of Re-LPS preparation in the diagnosis of chlamydial infection

A. Nongonococcal urethritis (NGU)

The antibody titers were determined in paired acute and convalescent sera obtained from 17 patients with NGU using the EIA method (Example 2A). Chlamydiae isolation was positive in all patients. The antibody response was considered positive if the antibody titer showed a 2 fold increase or decrease between the paired sera, or if IgM and/or IgA antibodies were found in the acute phase serum. The results of antibody determinations in NGU patients using the EIA are shown in Table VII.

TABLE VII

EIA antibody titers measured with Re-LPS in paired sera from NGU patients with positive chlamydiae culture.

| Criteria of positive antigen response | No. of patients | No. of positive findings | | | |
|---|---|---|---|---|---|
| | | IgG | IgA | IgM | Total |
| Titer change (paired sera) | 17 | 13 | 13 | 13 | 15 |
| IgM or IgA demonstrable in acute serum | 17 | | 15 | 14 | 17 |

Serological diagnosis was achieved in all patients in which chlamydiae has been isolated, either by demonstration of change in antibody titer and/or demonstration of acute phase antibodies of immunoglobulin class IgM and/or IgA.

B. Pelvic inflammatory disease (PID)

Paired serum samples from 8 PID patients, and acute sera from 5 PID patients with positive chlamydiae culture were tested using the EIA method, with Re-LPS from *S. typhimurium* SL 1102 as the antigen. In all cases, a serological diagnosis was possible either on the basis of antibody titer change, or demonstration of acute phase antibodies of the immunoglobulin classes IgA and/or IgM.

The Re-lipopolysaccharide mutants have been deposited under strain numbers SL 1102, SH 320, EH 237 and EH 193 with the National Public Health Institute, Mannerheimin-tie 166, SF-00280 Helsinki 28, Finland. *S. typhimurium* rough mutant of chemotype Re(SL 1102), obtained from B.A.D. Stocker and described by Wilkinson et al. in the *Journal of General Microbiol,* Vol. 70, pp. 527–554 (1972), was deposited with NPHI in May 1969. *S. minnesota* mutant mR595 (SH 320), obtained from Luderitz et al. and described by Luderitz et al. in the *Annals of N.Y. Academy of Sciences,* Vol. 133, pp. 349–374 (1966), was deposited with NPHI in November 1966. *Escherichia coli mutant D21f2* (EH 237), obtained from K. Jann and described by Mayer et al. in the *European Journal of Biochem.,* Vol. 66, pp. 357–368 (1976), was deposited with NPHI in November 1981. *Proteus mirabilis* mutant R45 (EH 193), obtained from K. Kotelko and described by Kotelko et al. in the *Journal of Hyg. Epidemiol. Microbiol. Immunol.,* Vol. 21, pp. 271–284 (1977), was deposited with NPHI in January 1979.

We claim:

1. A preparation for diagnosing chlamydial infections which comprises a Re-lipopolysaccharide complexed to a carrier molecule to enhance immunological response, said Re-lipopolysaccharide being isolated from a Re-lipopolysaccharide mutant of a gram-negative bacterium, wherein said Re-lipopolysaccharide is capable of cross-reacting with chlamydial group-specific antibody as may be present in a tested patient fluid sample and thereby indicating the presence of such chlamydial group-specific antibody.

2. A preparation according to claim 1, wherein the Re-lipopolysaccharide comprises a lipopolysaccharide having a lipid A component and a KDO-oligosaccharide component containing two or three KDO-molecules, said Re-lipopolysaccharide having the structure

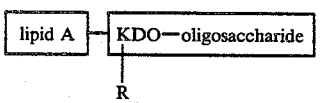

(I)

wherein the structures of lipid A and R vary in bacterial strains and wherein the structure of the KDO-oligosaccharide remains fairly constant.

3. A preparation according to claim 2, wherein the product represented as (I) is treated with a weak alkali and is capable of cross-reacting with chlamydial glycolipid.

4. A preparation according to claim 1, wherein the carrier molecule is a protein.

5. A preparation according to claim 4, wherein the protein carrier molecule is porin.

6. A method for detecting chlamydial infections, said method comprising the steps of:
   (a) contacting a given amount of a Re-lipopolysaccharide or an anti-Re-lipopolysaccharide antibody, said Re-lipopolysaccharide being isolated from a Re-lipopolysaccharide mutant of gram-negative bacteria, said anti-Re-lipopolysaccharide antibody being produced by immunizing animals with Re-lipopolysaccharide, with a sample to be assayed, and
   (b) assaying the contacted sample to determine whether the sample contains chlamydial group-specific antibody which cross-reacts with the Re-lipopolysaccharide or chlamydial group-specific antigen which cross-reacts with anti-Re-lipopolysaccharide antibody.

7. A method for detecting chlamydial infections according to claim 6, wherein the Re-lipopolysaccharide is treated with a weak alkali.

8. A method for detecting chlamydial infections according to claim 6, wherein the Re-lipopolysaccharide is used for the demonstration of chlamydial group-specific antibody by serological and immunological methods.

9. A method for detecting chlamydial infections according to claim 6, wherein the Re-lipopolysaccharide is treated with a weak alkali and is used for the demonstration of chlamydial group-specific antibody by serological and immunological methods.

10. A method for detecting chlamydial infections according to claim 6, wherein the Re-lipopolysaccharide is used for the detection of chlamydial group-specific antibody by enzyme immunoassay methods.

11. A method for detecting chlamydial infections according to claim 6, wherein the Re-lipopolysaccharide is treated with a weak alkali and is used for the detection of chlamydial group-specific antibody by enzyme immunoassay methods.

12. A method for detecting chlamydial infections according to claim 6, wherein the Re-lipopolysaccharide is used for the detection of chlamydial group-specific antibody by counterimmunoelectrophoresis methods.

13. A method for detecting chlamydial infections according to claim 6, wherein the Re-lipopolysaccharide is treated with a weak alkali and is used for the detection of chlamydial group-specific antibody by counterimmunoelectrophoresis methods.

14. A method for detecting chlamydial infections according to claim 6, wherein the Re-lipopolysaccharide is used for the detection of chlamydial group-specific antibody by double immunodiffusion methods.

15. A method for detecting chlamydial infections according to claim 6, wherein the Re-lipopolysaccharide is treated with a weak alkali and is used for the detection of chlamydial group-specific antibody by double immunodiffusion methods.

16. A method for detecting chlamydial infections according to claim 6, wherein the Re-lipopolysaccharide is used for the detection of chlamydial group-specific antibody by passive hemagglutination methods.

17. A method for detecting chlamydial infections according to claim 6, wherein the Re-lipopolysaccharide is treated with a weak alkali and is used for the detection of chlamydial group-specific antibody by passive hemagglutination methods.

18. A method for detecting chlamydial infections according to claim 6, wherein the Re-lipopolysaccharide is used for the detection of chlamydial group-specific antibody by hemolysis in gel methods.

19. A method for detecting chlamydial infections according to claim 6, wherein the Re-lipopolysaccharide is treated with a weak alkali and is used for the detection of chlamydial group-specific antibody by hemolysis in gel methods.

20. A method for detecting chlamydial infections according to claim 6, wherein the Re-lipopolysaccharide is used for the detection of chlamydial group-specific antibody by latex agglutination methods.

21. A method for detecting chlamydial infections according to claim 6, wherein the Re-lipopolysaccharide is treated with a weak alkali and is used for the detection of chlamydial group-specific antibody by latex agglutination methods.

22. A preparation for diagnosing chlamydial infections which comprises a antibody to the complex of a Re-lipopolysaccharide and a carrier molecule to enhance immunological response, said anti-Re-lipopolysaccharide complex antibody being produced by immunizing animals with Re-lipoplysaccharide complexed to a carrier molecule to enhance immunological response, and wherein said anti-Re-lipopolysaccharide complex antibody is capable of cross-reacting with chlamydial group-specific antigen as may be present in a tested patient fluid sample and thereby indicating the presence of such chlamydial group-specific antigen.

23. A preparation according to claim 22, wherein the Re-lipopolysaccharide comprises a lipopolysaccharide having a lipid A component and a KDO-oligosaccharide component containing two or three KDO-molecules, said Re-lipopolysaccharide having the structure

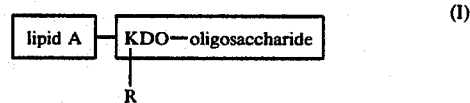

(I)

wherein the structures of lipid A and R vary in bacterial strains and wherein the structure of the KDO-oligosaccharide remains fairly constant.

24. A preparation according to claim 23, wherein the product represented as (I) is treated with a weak alkali and is capable of cross-reacting with chlamydial glycolipid.

25. A preparation according to claim 22, wherein the carrier molecule is a protein.

26. A preparation according to claim 25, wherein the protein carrier molecule is porin.

* * * * *